United States Patent [19]
Kim

[11] Patent Number: 5,888,056
[45] Date of Patent: Mar. 30, 1999

[54] DIAPHRAGM PUMP

[76] Inventor: Seong-Cheol Kim, 55-235, Gonghang-dong Gangseo-gu, Seoul, Rep. of Korea

[21] Appl. No.: 886,225

[22] Filed: Jul. 1, 1997

[30] Foreign Application Priority Data

Jul. 3, 1996 [KR] Rep. of Korea ................. 1996 26856

[51] Int. Cl.⁶ .................................................. F04B 11/00
[52] U.S. Cl. ............................... 417/540; 417/312; 92/80
[58] Field of Search ...................... 417/540, 312, 417/413.1; 92/80, 82

[56] References Cited

U.S. PATENT DOCUMENTS

| | | | |
|---|---|---|---|
| 3,362,346 | 1/1968 | Bottoms et al. ..................... | 417/540 |
| 3,838,944 | 10/1974 | Kolfertz ............................. | 417/540 |
| 4,594,059 | 6/1986 | Becker .............................. | 417/540 |
| 4,721,444 | 1/1988 | Pareja ............................... | 417/540 |
| 5,183,185 | 2/1993 | Hutcheson et al. ................ | 417/540 |

*Primary Examiner*—Thomas E. Denion
*Attorney, Agent, or Firm*—Dann, Dorfman, Herrell and Skillman, P.C.; Henry H. Skillman

[57] ABSTRACT

A diaphragm pump having a simple structure for effectively preventing pulsation of liquid being discharged, which includes an air chamber connected to a head-side discharge hole of the diaphragm pump and having a discharge-side discharge hole, and thereby pipes are kept from being damaged by preventing the pulsation of the liquid, and the level of noisy can be reduced to a very adequate level.

9 Claims, 6 Drawing Sheets

DIAPHRAGM PUMP

BACKGROUND OF THE INVENTION

1. Field of the Invention

The present invention relates to a diaphragm, and more particularly to a diaphragm pump for effectively preventing pulsation of liquid by installing an air chamber on the side wall of the pump head, which is connected to a head-side discharge hole of the diaphragm pump and includes a discharge-side discharge hole.

2. Description of the Prior Art

Generally, a typical diaphragm pump pumps liquid by converting rotational movement of a motor into a reciprocating movement by devices such as a cam. Since the amount of the discharged liquid from the diaphragm pump fluctuates by very small volume, the diaphragm pump is generally used for precisely instilling liquid chemicals or medicines.

FIGS. 1A to 1E are cross sectional views illustrating one embodiment of a conventional diaphragm pump. As shown in FIG. 1A, a diaphragm 110 is supported by a support ring 120 to form a pump chamber 130 in an opening area of a pump head 100. A suction hole 105 and a discharge hole 106 are located at the upper portion and the lower portion of a body 102, respectively.

The suction hole 105 and the discharge hole 106 are opened/closed by a check ball 140. Referring to FIG. 1C, an opening-side valve seat 141 having a cross-shaped groove is formed on a suction end of the suction hole 105 of the pump head 100 and an end of a discharge-side connector 160. And, a closing-side valve seat 142 having tapered shape is formed at an end of a suction connector 150 and a discharge side of the discharge hole 106 of the pump head 100.

The following describes the operation of the diaphragm pump constructed in such a manner as mentioned above.

When a motor (not illustrated) is driven to operate the pump, the rotational movement of the motor is changed to the reciprocating movement of a diaphragm shaft 111 by devices such as an eccentric cam, and thereby the diaphragm 110 is driven back and forth. FIG. 1A illustrates a state of the diaphragm being driven back, that is, a suction process, and FIG. 1B illustrates a state of the diaphragm being driven forward, that is, a discharge process.

During the suction process, due to the internal pressure, each check ball 140 of the suction side and the discharge side moves toward the center of the pump head 100. Subsequently, since there is the opening-side valve seat 141 is formed at the end of the suction hole 105 of the pump head 100, liquid is drawn to the pump chamber 130 through the cross-shaped groove. And, the discharge hole 106 is closed by the check ball 140. On the other hand, during the discharge process, each check ball 140 moves away from the pump head 100 to the outside such that the suction hole 105 is closed and only the discharge hole 106 is opened. Subsequently, the liquid in the pump chamber 130 is discharged through the cross-shaped groove formed at the discharge-side connector 160.

The advantage of such a conventional diaphragm pump in the long term is that the average amount of the discharged liquid is very constant. However, since the pumping operation is separated into the suction process and the discharge process, and it is intermittently performed, there is a fundamental problem of a pulsation of the discharged liquid, as shown in FIG. 1D.

In order to prevent such a pulsation of the discharged liquid, two or more pumps are connected in parallel and operated in different strokes, as shown in FIG. 1E. Referring to FIG. 2, another method is explained. By installing an air chamber 200 at the center of a liquid pipe passage, during the discharge process, the air in the air chamber 200 is pressurized, and thereby the amount of the discharging liquid from a discharge pipe 210 is reduced. During the suction process, due to the expansion force of the pressurized air, the liquid stored in the air chamber 200 during the discharge process is discharged through the discharge pipe 210. For reference, the unmentioned reference numeral 201 is a pressure gauge.

However, the benefit of using two more pumps being connected in parallel is significantly offset by the substantial increase in installation cost. Moreover, in the case of installing the air chamber at the center of the liquid pipe passage, it is difficult to perform the installation operation. Also, it is unsuitable to establish the air chamber when the connector of the pump or the liquid pipe passage is made of tube type. Furthermore, damages to the connector caused by the vibration of the air chamber when operating the pump are frequently occurred. Furthermore, since such methods cannot fundamentally remove the pulsation of the discharged liquid, water hammering caused by the pulsation can be generated and it may destroy pipes, especially, at high pressure.

SUMMARY OF THE INVENTION

Therefore, it is an object of the present invention to provide a diaphragm pump having a simple structure for efficiently preventing the pulsation of a discharged liquid.

In order to accomplish the above-mentioned object, the diaphragm pump in which the discharge of the liquid is intermittently carried out, includes: a first body having a diaphragm inside and including a first discharge hole and a suction hole; and a second body having a cavity being connected to the first discharge hole, and a second discharge hole for connecting the cavity and the outside, and attached to the side wall of the first body.

Preferably, the second discharge hole is formed inside of a discharge-side connector which is connected to the second body, and diameter of the exit area of the second discharge hole is smaller than that of the entrance area.

The diaphragm pump, preferably, further includes a cylindrical partitioning plate which is formed at the cavity to partition off the cavity of the second body, and having the lower portion opened. More preferably, the partitioning plate and the second body are integrally formed at the outer surface of the side wall of the first body of a pump head. Moreover, the diaphragm pump further includes a discharge pipe which is established inside of the cavity and connected to the second discharge hole.

BRIEF DESCRIPTION OF THE DRAWINGS

The above object and advantages of the present invention will be more clearly understood from the following detailed description taken in conjunction with the accompanying drawings, in which.

DETAILED DESCRIPTION OF THE PREFERRED EMBODIMENTS

The objects, characteristics and advantages of the above-described invention will be more clearly understood via the preferable embodiments shown in the attached drawings.

Figure 1A:
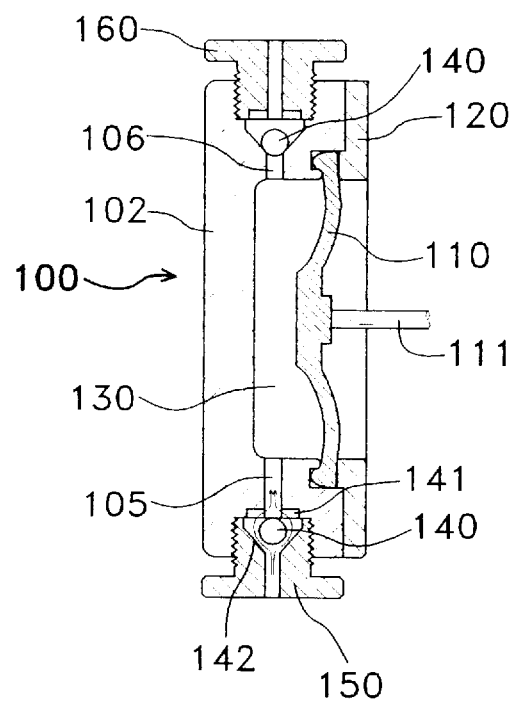
FIGS. 1A and 1B are cross sectional views showing the structure and operation of a conventional diaphragm pump.
Figure 1B:
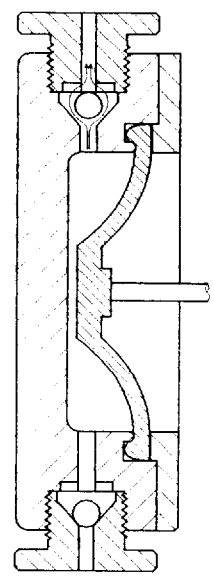
Figure 1C:
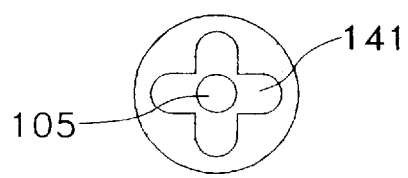
FIG. 1C is a plan view of an opening-side valve seat having a cross-shaped groove.
Figure 1D:
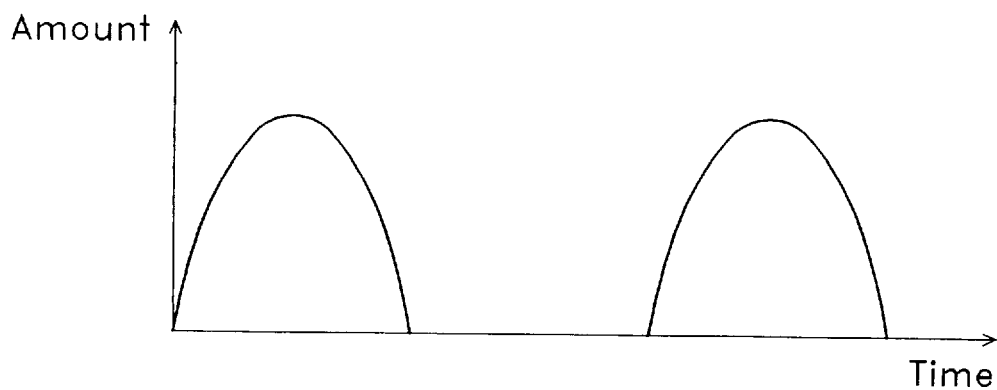
FIG. 1D is a graph showing a pulsation of the amount of discharged liquid.
Figure 1E:
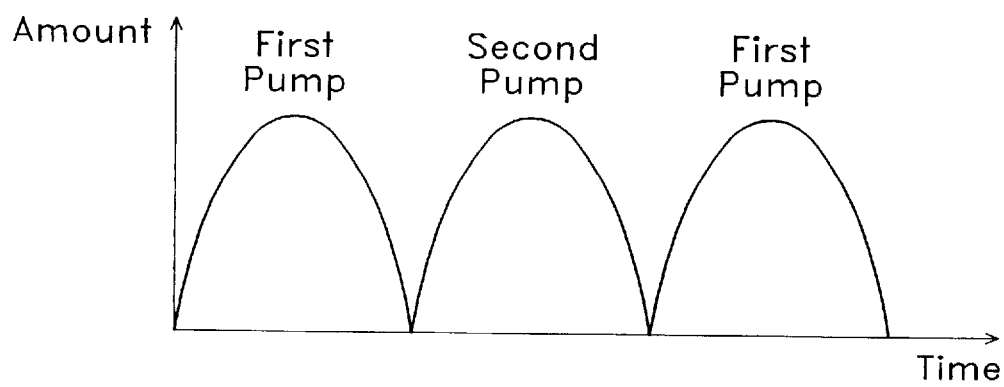
FIG. 1E is a graph showing a pulsation of the amount of the discharged liquid in the case of reducing the pulsation effect.
Figure 2:
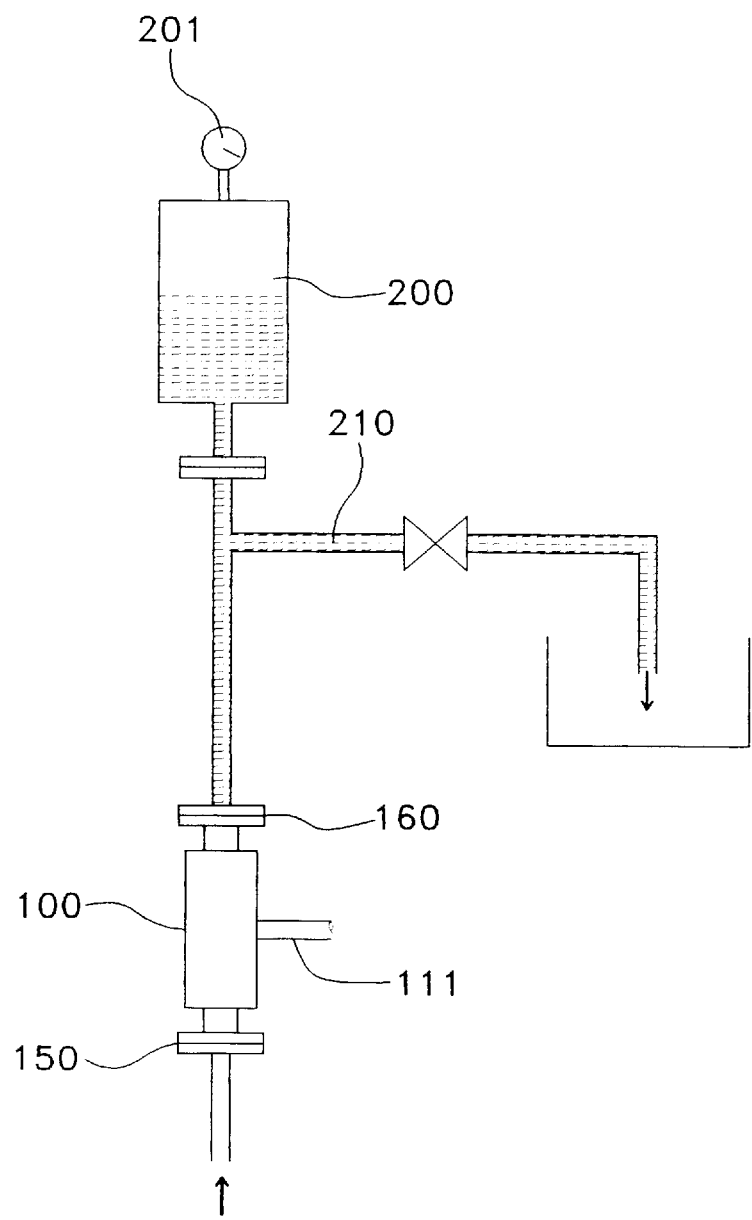
FIG. 2 is a schematic view showing an air chamber being installed on a conventional liquid pipe passage.
Figure 3A:
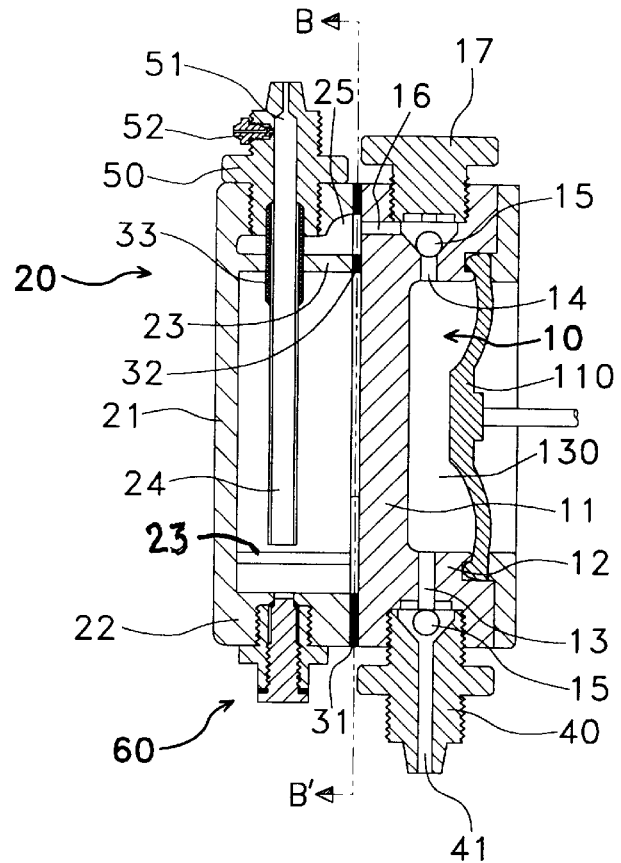
FIG. 3A is a cross sectional view of a diaphragm pump according to a preferred embodiment of the present invention.
Figure 3B:
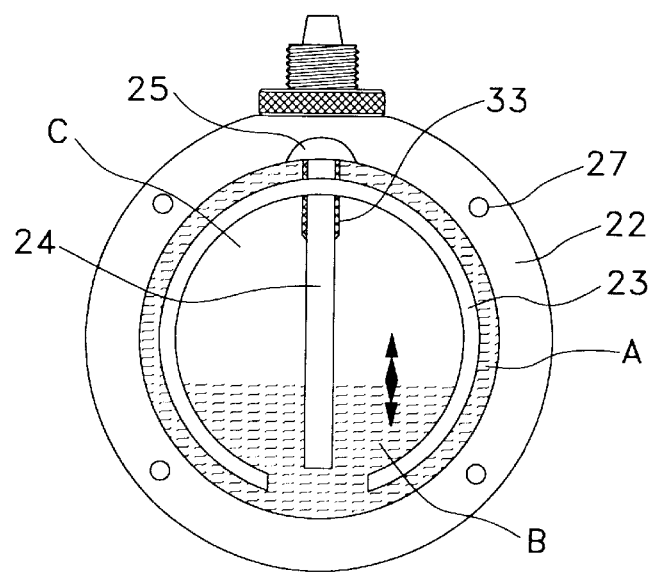
FIG. 3B is a front elevational view of an air chamber cut from the line B to B' of FIG. 3A.

FIGS. 3A and 3B illustrate the structure and operation of the diaphragm pump according to one embodiment of the present invention. FIG. 3A is a cross sectional view of main parts, and FIG. 3B is a front elevational view of an air chamber.

According to the drawings, a suction hole 13 and a head-side discharge hole 14, which are closed and opened by a check ball 15, are respectively formed at the upper and lower portions of a body 12 of a pump head 10. A suction-side connector 40 having a suction passage 41 is attached to the outside of the suction hole 13. Moreover, a cap 17 is connected to the outside of the head-side discharge hole 14.

An air chamber 20 is installed at a side wall 11 of the pump head 10 such that the air chamber 20 is connected to the head-side discharge hole 14 via a connecting hole 16 formed at the side wall 11 of the pump head 10 and a connecting groove 25 formed at one side of a body 22 of the air chamber 20. However, the connecting groove 25 can be selectively removed when the inner side wall of the body 22 is placed outside of the connecting hole 16 by increasing the internal diameter of the air chamber 20.

On the side wall 21 of the air chamber 20, a cylindrical partitioning plate 23, of which the lower portion is opened, is formed. A discharge-side connector 50 having a discharge-side discharge hole 51 is attached to the upper portion of the body 22. Consequently, the diameter of the exit side of the discharge hole 51 is smaller than that of the entrance side of the discharge hole 51. Though the lower portion of the partitioning plate 23 is exposed as it is opened over the whole width, a circular shape is preferred for much simpler manufacturing.

At the lower portion of the discharge-side connector 50, a discharge pipe 24, which is pressure-fixed by using a packing 33 as an intermediary, penetrates the partitioning plate 23 extending to the lower portion of the air chamber.

Among the unmentioned reference numerals in the drawing, reference numerals 31 and 32 are packings for preventing flowing of air and liquid. Reference numeral 27 is a bolt hole for fixing the air chamber to the pump head. Finally, reference numerals 60 and 52 are a drain valve and an air vent valve, respectively.

The following describes the operation of the diaphragm pump formed as the above-mentioned embodiment.

The state of the air chamber 20 in operation is shown in FIG. 3B. Specifically, the liquid to be pumped is filled in a space A and a space B. The space A is defined by the area in between the partitioning plate 23 and the body 22, and the space B is defined by the lower portion of the inside area of the partitioning plate 23. The air filled in a space C, which is defined by the upper portion of the inside area of the partitioning plate 23, is isolated from the external environment by the packings 32 and 33 and the liquid filled in the lower portion, and the amount of air filled in the space is always constant.

While the diaphragm 110 in a state of FIG. 3A moves up, that is, in the discharge process, the discharge-side check ball 15 moves up to open the head-side discharge hole 14. Simultaneously, the liquid previously flown to a pump chamber 130 during a previous suction process is discharged to the inside of the air chamber 20 via the head-side discharge hole 14 and a connection hole 16. Subsequently, as the liquid pressure increases inside the air chamber 20, the air in the space C is pressurized, thus the level of liquid filled in the inside the partitioning plate 23 rises. In other words, all of the liquid flown to the air chamber 20 via a connection pipe is not discharged through a discharge pipe 24 and the discharge-side discharge hole 51. As a certain amount of liquid influences a rising level of the liquid inside of the partitioning plate 23 and an increasing air pressure, a sudden change in the amount of liquid being discharged can be prevented.

On the other hand, during the suction process, the head-side discharge hole 14 is closed to prevent inverse flowing of liquid inside of the air chamber 20, and liquid discharging to the air chamber 20 is stopped. However, due to the air pressure inside of the air chamber 20 which is pressurized during the previous discharge process, the liquid inside of the air chamber 20 is continuously discharged through the discharge pipe 24 and the discharge-side discharge hole 51, and the liquid level inside of the partitioning plate 23 gradually decreases. Accordingly, the amount of the discharged liquid is not decreased rapidly, and it is almost equal to the amount of the liquid during the discharge process.

Furthermore, since the diameter of the exit area of the discharge-side discharge hole 51 is smaller than that of the entrance area, even if there is a small change in amount of the discharged liquid through the discharge pipe 24, the amplitude of the change decreases as passing through the exit area having a smaller diameter. Therefore, the pulsation effect of the discharged liquid is further reduced.

Figure 4A:
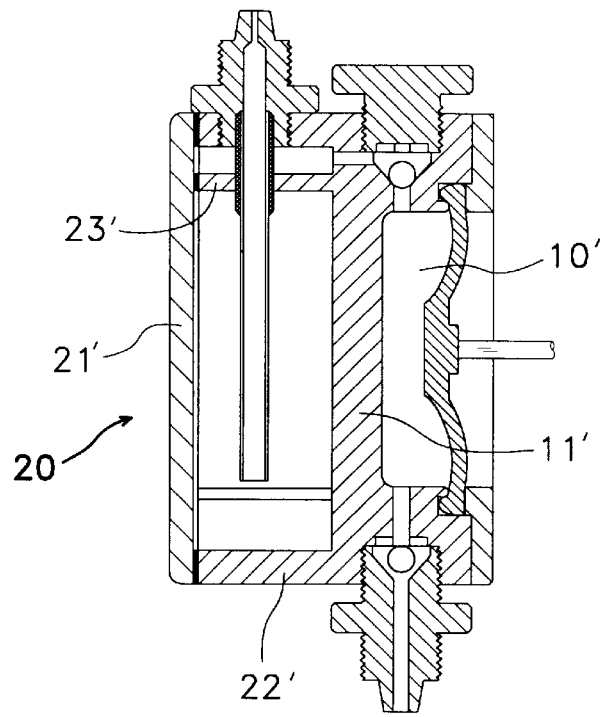
FIGS. 4A and 4B are cross sectional views of another preferred embodiments of the present invention.
Figure 4B:
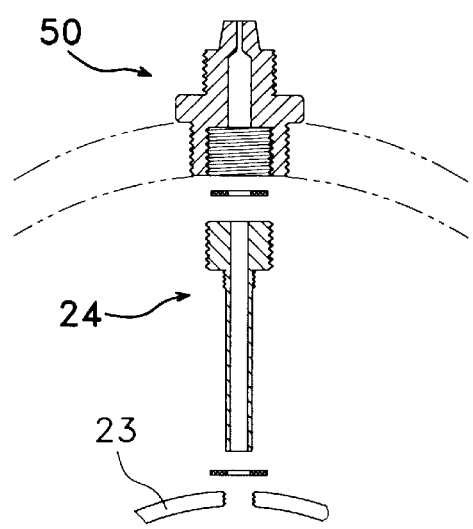

FIGS. 4A and 4B are sectional views showing another embodiments of the present invention. According to FIG. 4A, the partitioning plate 23 and the body 22 of the air chamber 20 are integrally formed at the side wall 11 of the pump head 10, and a side wall 21 separately formed is connected to the opened area. The discharge pipe 24 is fixed to the discharge-side connector 50 and the partitioning plate 23 by means of screws, as illustrated in FIG. 4B.

Figure 5A:
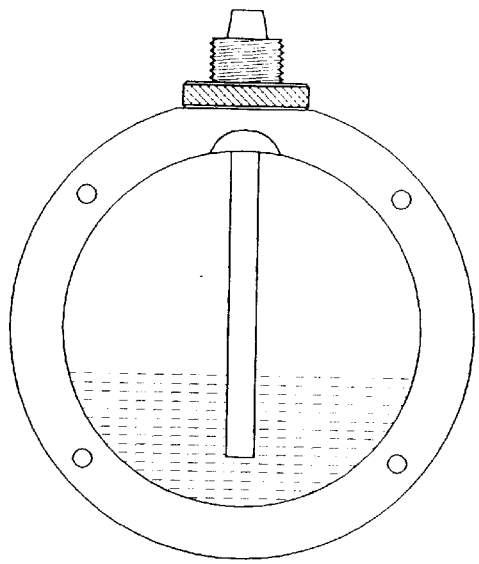
FIGS. 5A to 5D are elevational views of yet another preferred embodiments of the present invention.
Figure 5B:
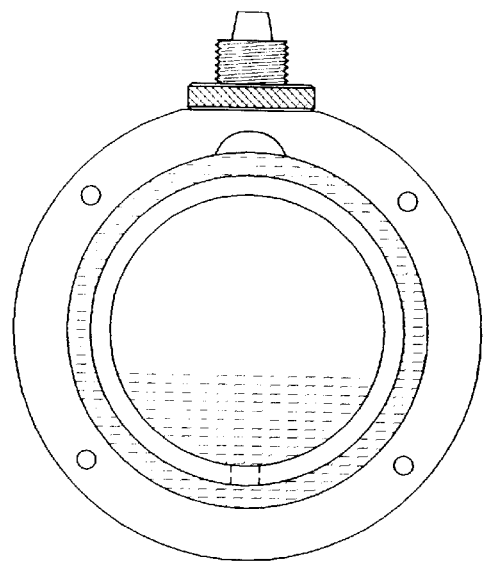

FIGS. 5A to 5D are sectional views illustrating another embodiments of the present invention. FIGS. 5A and 5B illustrate preferred embodiments having the discharge-side discharge hole formed at the upper portion of the air chamber. Referring to FIG. 5A, the partitioning plate is removed, and the liquid to be pumped which is in the lower portion of the air chamber is discharged to the discharge-side discharge hole of the upper portion of the air chamber through the discharge pipe.

Figure 5C:
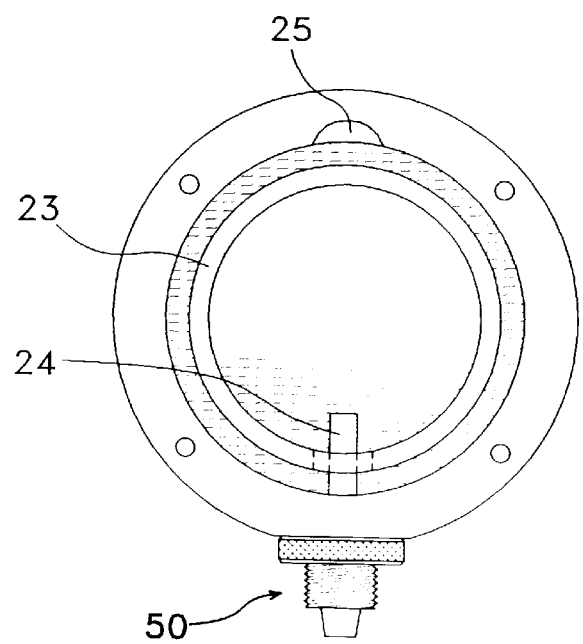
Figure 5D:
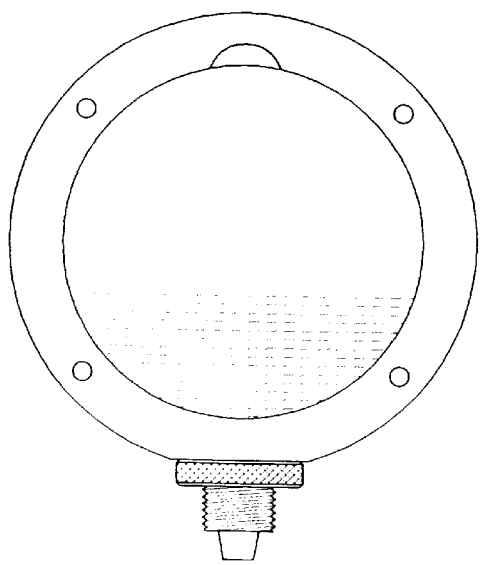

Referring to FIG. 5B, in the case that the partitioning plate is installed, as the discharge-side discharge hole is contacted with the liquid to be pumped outside of the partitioning plate instead of the air, the discharge pipe can be removed. FIGS. 5C and 5D illustrate preferred embodiments showing the discharge-side discharge hole formed at the lower portion of the air chamber. Referring to FIG. 5C, the connecting groove 25 is formed at the upper portion of the air chamber, and the discharge-side connector 50 and the discharge-side discharge hole are formed at the lower portion of the air chamber, respectively. The partitioning plate 23 and the discharge pipe 24 are also provided.

Referring to FIG. 5D, in the case that the discharge-side discharge hole is formed at the lower portion of the air chamber, as the discharge-side discharge hole is directly connected with the liquid to be pumped without a separate partitioning plate, the partitioning plate and the discharge pipe can be removed.

The operating principle of the above-mentioned embodiments is similar to that of the embodiments of FIG. 3, and the detailed description is omitted.

When the partitioning plate is removed as in case of FIG. 5A or FIG. 5C, a small amount of air can be slipped into the pump chamber through the connection hole during closing action of the check ball according to the suction process. However, as the liquid is flown through the suction hole during the suction process, even if a small amount of air is escaped from the air chamber to the pump chamber, the air will be unable to slip through the suction hole. During the next discharge process, the air will be discharged back to the air chamber along with the liquid. Therefore, the amount of air loss in the air chamber caused by such a leakage is insignificant.

As described above, the diaphragm pump of the present invention proficiently prevents the pulsation effect of the discharged liquid. Moreover, since there is no need for installing extra parts, such as an air chamber and pipes, the installation of the pump becomes much easier, thereby reducing the installation cost.

Furthermore, even if the air chamber is installed to reduce the pulsation of liquid according to the conventional method, the liquid is still discharged intermittently from a diaphragm pump. As a result, the conventional diaphragm pump is noisy, and the pipes are frequently damaged due to the water hammering. However, since the diaphragm pump of the present invention reduces the pulsation of the liquid with the pump itself before discharging the liquid, the pipes are guarded from such damage, and the level of noisy can be reduced to a very adequate level.

Even though the present invention has been described in application to a certain type of a diaphragm pump for convenience, it should be noted that the present invention can be applied to any other type of diaphragm pumps or any other type of pumps in which the pulsation of the liquid is occurred by the intermittent suction and discharge.

While the present invention has been described in connection with preferred embodiments, various modifications and equivalent arrangements can be made without violating the scope and spirit of the invention. For example, the connection hole can be replaced with a separate pipe, or the shape of the partitioning plate or the discharge-side connector can be modified.

What is claimed is:

1. A diaphragm pump which pumps liquid intermittently, comprising:

a first body having a side wall, an upper side and a lower side, a first discharge hole formed through said upper side and a suction hole formed through said lower side, and a diaphragm installed in said first body; and a second body mounted on said side wall of said first body and including:

a cavity connected to said first discharge hole; and a second discharge hole for communicating with external environments; and a cylindrical partitioning plate formed inside of said cavity for partitioning said cavity into an internal cylindrical chamber part and an external chamber part surrounding said cylindrical chamber part, said partition having a lower portion opened to afford liquid communication between said internal and external chamber parts.

2. The diaphragm pump of claim 1, having a discharge connector coupled with said second body, said second discharge hole being formed in said discharge connector.

3. The diaphragm pump of claim 1, wherein said second discharge hole includes an exit end and an entrance end, said entrance end having a larger diameter than said exit end.

4. The diaphragm pump of claim 1, further comprising a discharge pipe open at one end in said cavity and connected at the opposite end to said second discharge hole.

5. The diaphragm pump of claim 1, wherein said cylindrical partitioning plate is integrally formed with said second body and is sealed to said first body.

6. The diaphragm pump of claim 1, wherein said cylindrical partitioning plate is integrally formed with said first body and is sealed to said second body.

7. The diaphragm pump of claim 1, wherein said first discharge hole is connected to said cavity to provide a liquid level in one of said chamber parts with an air pocket above said level and liquid below said level, said second discharge hole communicating with said one chamber part below the liquid level.

8. The diaphragm pump of claim 7, wherein said one chamber part is said internal cylindrical chamber part, and said external chamber part is filled with liquid and surrounds said air pocket.

9. A diaphragm pump which pumps liquid intermittently, comprising:

a first body having a first discharge hole, a suction hole, a diaphragm installed in said first body, and means to displace said diaphragm back and forth to pump liquid flow in through said suction hole and out through said first discharge hole;

a second body mounted on said first body and said second body including:

a cavity connected to receive liquid flowing out through said first discharge hole; and a second discharge hole for communicating with external environments; and a cylindrical partitioning plate formed inside of said cavity for partitioning said cavity into an internal cylindrical chamber part and an external chamber part surrounding said internal cylindrical chamber part, said partition having a lower portion open to afford liquid communication between said internal and external chamber parts to provide a liquid level in one of said chamber parts with liquid below said level and an air pocket above said level, said first discharge hole communicating with said one chamber part through the other of said chamber parts, so that when liquid is pumped into said cavity it elevates the air pressure in said pocket, said second discharge hole communicating with said one chamber part below the liquid level, so that the elevated air pressure in the pocket discharges liquid through said second discharge hole.

* * * * *